US012788344B2

(12) United States Patent
Carelsen et al.

(10) Patent No.: US 12,788,344 B2
(45) Date of Patent: Nov. 10, 2026

(54) RENAL DENERVATION ABLATION MONITORING USING PERFUSION ANGIOGRAPHY

(71) Applicant: KONINKLIJKE PHILIPS N.V., Eindhoven (NL)

(72) Inventors: Bart Carelsen, Eindhoven (NL); Jim Reekers, Eindhoven (NL); Iris Ter Horst, Eindhoven (NL); Arjen Van Der Horst, Tilburg (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 126 days.

(21) Appl. No.: 18/989,762

(22) Filed: Dec. 20, 2024

(65) Prior Publication Data

US 2025/0120662 A1 Apr. 17, 2025

Related U.S. Application Data

(63) Continuation of application No. 17/768,099, filed as application No. PCT/EP2020/077157 on Sep. 29, 2020, now Pat. No. 12,171,603.

(30) Foreign Application Priority Data

Oct. 14, 2019 (EP) .................................... 19202890

(51) Int. Cl.
*A61B 6/00* (2024.01)
*A61B 90/00* (2016.01)

(52) U.S. Cl.
CPC .............. *A61B 6/481* (2013.01); *A61B 6/487* (2013.01); *A61B 6/5217* (2013.01); *A61B 90/37* (2016.02); *A61B 2090/376* (2016.02)

(58) Field of Classification Search
CPC .......... A61B 2018/00577; A61B 18/04; A61B 18/1492; A61B 2017/00084; A61B 2017/00106; A61B 2017/0011; A61B 2017/00292; A61B 2018/00011; A61B 2018/0016; A61B 2018/00178; A61B 2018/00267; A61B 2018/00279;
(Continued)

(56) References Cited

U.S. PATENT DOCUMENTS

2013/0116496 A1 5/2013 Waksman
2016/0113699 A1* 4/2016 Sverdlik .................. A61N 7/00
606/27

FOREIGN PATENT DOCUMENTS

WO 2017100140 A2 6/2017
WO 2018204284 A1 11/2018

OTHER PUBLICATIONS

International Search Report and Written Opinion of PCT/EP2020/077157, dated Dec. 1, 2020.

* cited by examiner

*Primary Examiner* — Dani Fox

(57) ABSTRACT

An apparatus for providing patient selection and treatment guidance for ablation treatments, in particular renal denervation treatment, is provided which is adapted to derive, from two time series of diagnostic images indicative of two states of the patient, two dynamics measures in order to determine at least one index indicative of the relative difference between the first state and the second state. Based on the at least one index, it is possible to track the progression of the ablation treatment and determine if it has been completed. Further, the index may be used to select likely responders to the ablation treatment.

11 Claims, 3 Drawing Sheets

(58) Field of Classification Search
CPC ........... A61B 2018/00434; A61B 2018/00511; A61B 8/06; A61B 8/08
See application file for complete search history.

RENAL DENERVATION ABLATION MONITORING USING PERFUSION ANGIOGRAPHY

CROSS-REFERENCE TO PRIOR APPLICATIONS

This application is a continuation of U.S. application Ser. No. 17/768,099, filed Apr. 11, 2022, now U.S. Pat. No. 12,171,603, which is the U.S. National Phase application under 35 U.S.C. § 371 of International Application No. PCT/EP2020/077157, filed on Sep. 29, 2020, which claims the benefit of European Patent Application No. 19202890.0, filed on Oct. 14, 2019. These applications are hereby incorporated by reference herein.

FIELD OF THE INVENTION

The present invention relates to an apparatus for providing treatment guidance for an ablation treatment a corresponding method and a respective computer program. In particular, the present invention relates to an apparatus and a method for providing treatment guidance and patient selection for a renal denervation treatment employing ablation of the nerves on the vessel wall of the renal artery.

BACKGROUND OF THE INVENTION

Hypertension (HTN), commonly known as high blood pressure, is a long-term medical condition which is a major risk factor for coronary arteries disease, heart failures, peripheral arterial diseases and the like. Thus, it is of vital importance to appropriately treat such hypertension to reduce the risks that the patient may develop further ailments caused by it.

Typically, hypertension is treated by controlling the blood pressure by means of respective antihypertensive medication, often accompanied by having the patient perform necessary modifications to his or her lifestyle. However, in the case of resistant hypertension, the blood pressure remains above a certain target level albeit the patient having been treated by antihypertensive medication. Here, other treatment options are to be considered.

One such alternative treatment option is renal sympathetic denervation (RSDN), also called renal denervation (RDN). RDN is a minimally invasive endovascular catheter-based procedure which employs ablation techniques such as radiofrequency ablation, ultrasound ablation, alcohol ablation or the like. Hereby, the nerves in the vessel wall of the renal artery are ablated using the ablation procedure. This causes the reduction of sympathetic afferent and efferent activity to the kidney. This treatment takes into account the fact that the systemic vascular impedance is, amongst others, regulated by the renin-angiotensin system (RAS). The stimulation of the efferent activity causes increased activity of the RAS, renal sodium reabsorption and a reduced renal flow, whereas the stimulation of the afferent activity causes increased renal sympathetic outflow to peripheral organs such as the kidney, the heart and/or the peripheral vasculature. The afferent renal sympathetic nerve activity may modulated by the efferent renal sympathetic nerves via norepinephrine as neurotransmitter. Hereby, efferent renal sympathetic nerves activate $\alpha_1$- and $\alpha_2$-adrenoreceptors (sometimes commonly referred to as alpha receptors) on afferent renal nerves, which may increase and decrease afferent renal nerve activity, respectively. As a result, by reducing this activity, the blood pressure can be decreased.

However, the response of the blood pressure to RDN varies from patient to patient. That is, in some cases, patients have been shown to respond very positively by exhibiting a large decrease in blood pressure, in other cases, patients have shown actual increases in blood pressure in response to an RDN treatment. Thus, the success of the RDN treatment largely depends on an appropriate patient selection.

Further, the success of the RDN treatment depends on the extent of the ablation of the nerves in the vessel wall of the renal artery, i.e. on the completeness of the ablation procedure. Nowadays, treatment guidance for the ablation procedure is not commonly available. Thus, a user performing the ablation process, such as a physician, is not capable to track the progression of the ablation process and to know when it is completed.

US 2016/0113699 discloses a device and method for renal denervation, and discloses assessment of the treatment effectiveness by comparing responses to stimulation before and after the denervation treatment.

WO 2018/204284 discloses comparing blood perfusion levels before and after ablation to provide a metric for the progress of the ablation.

SUMMARY OF THE INVENTION

It is therefore an object of the present invention to provide an apparatus and a corresponding method for providing treatment guidance for an ablation procedure performed on the renal vessel walls of a patient.

It is a further object of the invention to provide an apparatus and a method for monitoring the ablation procedure and for determining when the ablation procedure has been completed. More particularly, it is an objection of the invention to provide an apparatus and a corresponding method for providing treatment guidance to a user performing a renal denervation (RDN) procedure by performing appropriate patient selection, monitoring the progression of the ablation procedure during the treatment and by indicating that the ablation procedure has been completed in order to terminate the treatment.

This objective is achieved by an apparatus for providing treatment guidance for an ablation treatment, comprising: an input unit adapted to receive a first time series of diagnostic images of a region of interest of a patient's vasculature, the first time series representing a first state, and a second time series of diagnostic images of the region of interest of the patient's vasculature, the second time series representing a second state, a processing unit adapted to derive, from the first time series of diagnostic images, a first dynamics measure indicative of a contrast agent dynamic through the region of interest over time for the first state, derive, from the second time series of diagnostic images, a second dynamics measure indicative of a contrast agent dynamic through the region of interest over time for the second state, and determine, based on the first dynamics measure and the second dynamics measure, at least one index indicative of a relative difference between the first state and the second state, and an output unit adapted to output the at least one index to a user.

The apparatus for providing treatment guidance makes use of the fact that the physiology of the vasculature changes during the ablation process. Specifically, when employing ablation on the nerves situated on the vessel wall of the arteries that are treated, the microvascular impedance will be reduce. This allows a fluid, typically the blood, to flow faster through the artery. This means, by tracking the fluid flow through the vasculature, the progression of the ablation treatment may be tracked. Since it is rather difficult to measure the blood flow velocity itself, this tracking is performed by introducing a traceable fluid, such as a contrast agent, into the arteries and tracking said traceable fluid by a non-invasive imaging modality allowing to visualize the traceable fluid.

In this context, the term treatment guidance may particularly refer to the provision of information as to the extent of the ablation performed by an ongoing ablation treatment, i.e. the progression of the ablation treatment, as to whether or not an ablation treatment has been completed and as to whether or not a patient is a likely responder to the ablation treatment. This allows to improve the treatment process by being able to determine its progress, its end point—and, therefore, its success—and by improving patient selection such as to avoid unnecessary treatments to patients that would likely not respond to the treatment anyway.

Further, the terms first time series of diagnostic images and second time series of diagnostic images may particularly refer to a plurality of diagnostic images that may have been obtained using a specific imaging modality that may visualize the contrast agent within a region of interest. Hereby, each diagnostic image of the time series corresponds to a particular point in measurement time. This allows to track dynamic processes, such as the evolution of contrast agent through the vasculature presented in the diagnostic image.

In that context, the term diagnostic image may particularly refer to an image representing the region of interest in the patient's vasculature. Hereby, the term vasculature may refer to a vessel tree or a single vessel. In some embodiments, the diagnostic images may represent a vessel of interest that is part of the renal arteries. That is, the region of interest used for the first time series of diagnostic images and/or the second time series of diagnostic images is placed on the kidney of the patient.

In some embodiments, the first time series of diagnostic images and/or the second time series of diagnostic images may be obtained by a diagnostic imaging modality that allows to visualize the contrast agent in the arteries. Suitable diagnostic imaging modalities may particularly include X-ray imaging modalities.

The diagnostic imaging modality may particularly be gated. Hereby, the gated diagnostic imaging modalities may typically employ a gated reconstruction, in which the acquisition of the diagnostic images is performed in parallel with acquisition of data providing information over the cardiac cycle, such as electrocardiogram (ECG) or photoplethysmographic (PPG) data. This data may hereby be used to gate the image acquisition and the reconstruction by means of respectively selected phase points of the cardiac cycle.

The first and second time series of diagnostic images may represent a first and a second state for the ablation treatment, respectively. Hereby, the first and second state may particularly correspond to a state indicative of the progress of the ablation treatment and a respective reference state. The reference state corresponds to a state indicative of the expected/desired result of the ablation treatment.

Specifically, in some embodiments the first state may correspond to a patient-specific state. The second state may correspond to a reference state providing a reference in order to determine the effect of a (potential) ablation treatment.

The patient-specific state and the reference state may hereby particularly be selected based on the kind of treatment guidance that is desired. Hereby, different combinations of patient-specific states and reference states are possible.

In case the treatment guidance desired relates to an appropriate patient selection, in some embodiments, the patient-specific state may correspond to a state for the patient prior to the ablation treatment "as is", i.e. a baseline acquisition that is indicative of the microvascular function of the renal arteries for that particular patient without any medication administration and/or ablation treatment having been performed yet.

In these embodiments, the reference state may particularly correspond to a state that has been derived from a clinical study. In some embodiments, the state derived from clinical studies is particularly representative of the desired result of the ablation treatment. In this case, the reference state may correspond to a general reference state used for all patients or for all patients of a particular patient group (such as same age, same gender, et cetera). In these embodiments, the reference state may also correspond to a state of a patient who has been administered alpha blockers, i.e. who has received medication which block alpha receptor stimulation and therefore vasoconstriction. This state is typically also derived prior to the ablation treatment. Using medication administration allows to provide a reference state that is indicative of the effect that the ablation of the nerves in the renal arteries would have for that particular patient. Hence, the reference state does not correspond to a general reference state used for all patients, but to a reference state that is derived for each patient individually.

In these embodiments, where the first state corresponds to a baseline state and the second state corresponds to a state that provides reference to the desired result of the ablation process, it may be determined that the patient is suitable for ablation treatment for the purpose of renal denervation if the difference between the first dynamics measure for the first state and the second dynamics measure for the second state is large, which may particularly be expressed by the respective index indicative of the difference. This means that the effect of the renal denervation may be large as well, thereby resulting in a significant reduction of the microvascular impedance in case of a successful treatment and, accordingly, a reduction of the hypertension for that patient.

In some embodiments where the treatment guidance desired relates to an appropriate patient selection, it may also be the patient-specific (first) state that corresponds to a state of the patient after administration of alpha blockers, whereas the reference state may be a general reference state that has been derived from a clinical study. As indicated here above, the administration of medication blocking the alpha receptors simulates the effect that the ablation of the nerves in the renal arteries would have. Accordingly, a patient may also be selected by determining a first dynamics measure for a first state including medication administration and comparing it to a second dynamics measure for a second state indicative of the desired result to be achieved by the ablation procedure, i.e. indicative of a state in which the microvascular impedance has been appropriately reduced.

In this case, a patient may be considered as suitable for the ablation treatment in case the difference indicated by the index is small. This means that the patient would indeed be susceptible to an ablation of the nerves leading to a reduction in the microvascular impedance.

In case the treatment guidance desired relates to a tracking of the progression of the ablation treatment and/or to the determination as to whether or not an ablation treatment has been completed, the patient-specific state may particularly correspond to a state for the patient prior to and/or during and/or after the ablation treatment. That is, in case of treatment guidance for an ongoing ablation treatment, the patient-specific (first) state may correspond to a current state of the patient that is subjected to the ablation treatment. In these cases, the reference state may, again, correspond to a state that has been derived from clinical studies. In some embodiments, the state that has been derived from clinical studies may particularly be a state that is representative of the desired outcome of the ablation treatment. In some embodiments, multiple first time series of diagnostic images may be obtained during the ongoing ablation treatment, such as to derive multiple first dynamics measures, each of which used to iteratively provide an indication of a (new) current state of the patient. By comparing the thus determined current first dynamics measure to the dynamics measure of the reference state from clinical studies, the progression of the ablation treatment may be tracked.

In some embodiments, the reference state may also correspond to a state of a patient who has been administered alpha blockers, i.e. who has received medication which block the vasoconstrictive effect of alpha receptor stimulation. In this case, the reference state also indicates the desired outcome of the ablation treatment. That is, by comparing the second dynamics measure for the thus defined reference state to the first dynamics measure for the first state that is iteratively updated during the ablation treatment, the progression of the ablation treatment may likewise be tracked.

That is, in the above-cited embodiments in which the reference state corresponds to a state indicative of the desired outcome of the ablation treatment, the first dynamics measure of the first state should, during the ablation treatment, approach the second dynamics measure of the reference state. Once the difference between the first and the second dynamics measure becomes minimal (i.e. the states become very similar), the treatment may be deemed successful and may be terminated. Accordingly, by tracking the progression of the treatment, it may also be determined when the ablation treatment is completed.

Further, in some embodiments where the treatment guidance relates to a tracking of the progression of the ablation treatment and/or to the determination as to whether or not an ablation treatment has been completed, both, the first state used for a first assessment may be used as a reference state for a subsequent assessment. More specifically, in some embodiments, the first and second time series to derive the first and second dynamics measure may be acquired repeatedly, in particular in pre-defined intervals, during the ablation treatment. As an example, a second time series of diagnostic images may be acquired prior to the ablation treatment and a first time series of diagnostic images may be acquired after some (pre-defined) time period after starting of the ablation treatment. Then, the first and second dynamics measure derived for these time series, respectively, are compared to one another, resulting in an index indicative of the relative difference between the first and the second dynamics measure—and, as such, between the first and the second state—having a particular value. Subsequently, another first time series of diagnostic images may be acquired after another interval of the pre-defined time period has based, i.e. e.g. after twice the time period after starting of the ablation treatment. From this first time series, another first dynamics measure may be derived. For subsequent comparison, the dynamics measure derived from the previously determined first time series (i.e. the time series acquired after once the time period after starting of the ablation treatment) is deemed to correspond to the second dynamics measure, i.e. the state derived from the previously determined first time series is deemed the reference state. Then, the first dynamics measure and the second dynamics measure (the first dynamics measure from the past round) are compared and an index indicative of the relative difference between the first and second state is, again, determined. In case of a treatment progression, this index should be different from the previously determined index. This process may be repeated until the difference between the current index and the previously determined index is minimal nor non-existent, i.e. until there is no change between the current first state and the previous first state (used as the reference).

As indicated herein above, the first time series of diagnostic images may be used to derive a first dynamics measure indicative of the contrast agent dynamic through the region of interest for the first state. The second time series of diagnostic images may be used to derive a second dynamics measure indicative of the contrast agent dynamic through the same region of interest for the second state. Hereby, the first dynamics measure and the second dynamics measure are each representative of the flow dynamic of the flow through the artery that is treated by the ablation treatment and the vasculature behind the artery and, as such, for the physiology and, in particular, the (micro)vascular impedance.

The first dynamics measure and the second dynamics measure are hereby each derived over time. This allows to define the first and second dynamics measure for the first and the second state as a function of time each. This may particularly be achieved by determining a value for the first dynamics measure for each diagnostic image of the first time series and determining a value for the second dynamics measure for each diagnostic image of the second time series. These values as determined for the first dynamics measure and second dynamics measure, respectively, may then be analyzed as a function of time. This analysis allows for a better understanding of the contrast agent dynamics and, thus, of the flow dynamics through the artery that is treated and the vasculature in the periphery of the artery.

The first dynamics measure and the second dynamics measure may be used to determine at least one index indicative of a relative difference between the first state and the second state. In some embodiments, the at least one index may particularly be provided such as to be indicative of the difference between the state of the vasculature, such as the treated artery, prior to the treatment and the state of vasculature post-treatment. In some embodiments, the at least one index may be provided such as to indicate the difference between the state of the vasculature during the treatment and the state of the vasculature post-treatment or the state of the vasculature prior to the treatment. In some embodiments, the at least one index may also be used to indicate the difference between the state of the vasculature at the beginning of a pre-defined interval and at the end of a pre-defined interval during ablation treatment, whereby the index may be iteratively re-determined.

Alternatively or additionally, the at least one dynamics index may be provided such as to allow assessment of the status of the vasculature post-treatment without having regard of the status pre-treatment.

The at least one index shall be provided to a user, such as a physician, thereby allowing said user to visually assess the progression of the ablation treatment. This allows the user to draw conclusions on the progression of the treatment and/or to identify the treatment's end point. In some embodiments, the end point may be considered to correspond to a point at which the ablation treatment is deemed to be completed. In some embodiments, this point at which the ablation treatment is deemed to be completed may be determined by comparing the at least one index to a pre-defined threshold.

In some embodiments, where the second (reference) state corresponds to a state indicative of the desired outcome of the ablation treatment, as e.g. derived from clinical studies or on the basis of medication administration, in particular administration of alpha blockers, the treatment may be deemed complete if the at least one index indicative of the relative difference between the first state and the second state becomes minimal. In cases where the at least one index is between 0 and 1, this means that the at least one index would approach 0. In this case, a pre-defined threshold may be around 0,1, more particularly around 0.05, even more particularly around 0.02 relative difference. If the at least one index would be below these thresholds, the treatment would be deemed complete.

In some embodiments, where the second (reference) state corresponds to a state indicative of the patient's situation prior to the ablation treatment, as e.g. derived from a time series of diagnostic images acquired prior to the ablation treatment, the treatment may be deemed complete if the at least one index becomes maximal. In cases where the at least one index is between 0 and 1, this means that the at least one index would approach 1. In this case, a pre-defined threshold may be around 0.9, more particularly around 0.95, even more particularly around 0.98 relative difference. If the at least one index would be above these thresholds, the treatment would be deemed complete.

That is, in some embodiments, it may be determined that the ablation treatment has been completed if the index is below or above a given threshold value. In some embodiments, the determination of the end point may also be based on the determination that the ablation has not been successful. That is, in some cases, if, after a predetermined amount of time, no significant change in the contrast agent dynamic is registered, the treatment shall be deemed unsuccessful and shall accordingly be terminated. In some embodiments, the termination of the treatment may be performed manually by the user. In some embodiments the termination of the treatment may be performed automatically in response to a respective indication generated and output upon comparison of the index to the threshold value and respective determination that the ablation treatment may be considered completed.

In some embodiments, the first time series of diagnostic images and/or the second time series of diagnostic images is acquired using X-ray angiography. In some embodiments, the ablation treatment corresponds to a renal denervation (RDN) treatment.

X-ray angiography is a diagnostic imaging technique particularly well-suited to visualize blood vessels in the (human) body. X-ray angiography is typically performed by injecting a contrast agent into the blood vessels and subsequently irradiating the body part with the contrast agent-filled blood vessels with X-ray radiation to obtain a two-dimensional image in which the contrast agent-filled blood vessels are clearly visible. The diagnostic images of the first time series and/or the diagnostic images of the second time series may thus correspond to X-ray angiography images representing the region of interest in the patient's vasculature. Hereby, the usage of X-ray perfusion angiography is particularly well-suited for obtaining the first and second time series of diagnostic images.

In some embodiments, digital subtraction angiography (DSA) may be employed for determining the first and second time series of diagnostic images. DSA is a technique which employs a subtraction method of subtracting a diagnostic image obtained prior to injection of the contrast agent (a so-called mask) from a diagnostic image acquired once the contrast agent has entered the vessels. This allows to reduce the influence of bones and soft tissue surrounding the blood vessel and, thereby, to enhance visibility of the blood vessels. These highly visible blood vessels may then be removed to focus on the region of interest. Hereby, both the DSA approach as well as the subsequent removal of vessels other than the vessels in the region of interest may be performed using a classifier which has been trained with a respective ground truth. In some embodiments, the classifier may particularly comprise a deep neural network.

The apparatus for providing treatment guidance for an ablation treatment may particularly be used for providing treatment guidance of radiofrequency ablation or ultrasound ablation that is aimed at treating resistant hypertension. In some embodiments, the treatment guidance may also be provided for newly developing techniques such as alcohol ablation, cryo-ablation and/or microwave ablation or the like which may likewise be used for the treatment of resistant hypertension.

The ablation-based treatment of hypertension is based on the consideration that the sympathetic nervous system elicits its effect on the renal artery by stimulating the alpha receptors that cause vasoconstriction. Ablating the nerves in the wall of the renal artery using e.g. radiofrequency pulses or ultrasound (or any other ablation method) allowing to ablating the nerves results in a reduction of the renal sympathetic afferent and efferent activity, thereby releasing the vasoconstriction. This may result in a decrease in blood pressure.

Hereby, the employment of X-ray perfusion angiography may e.g. allow to visualize the time density curve for the contrast agent in the region of interest. This region of interest may hereby be situated on the kidney (i.e. the vasculature of the kidney) and/or over the renal artery. This would then allow to monitor the flow of contrast agent through the renal vasculature and/or renal artery over time during the ablation treatment. Now, if the ablation treatment on the renal artery is successful the flow of contrast agent will exhibit a different behavior than pre-treatment, as the denervation-caused vasoconstriction release means that the impedance is reduced. The peripheral impedance of the vessels, however, influences the flow of a fluid, such as the blood or the contrast agent, through the renal vasculature and/or renal artery. That is, by analyzing the dynamic behavior of the contrast agent flow over time, the effect of the denervation may be tracked. As a further benefit, since the acquisition of the time series of diagnostic images typically covers the entire kidney with the region of interest being positioned either over the entire kidney or a subsection thereof, this allows to analyze the dynamic behavior of the contrast agent in different regions, such as the renal cortex compared to the renal medulla.

In some embodiments, the apparatus further comprises a comparing unit, wherein the comparing unit is adapted to determine that the ablation treatment is completed by comparing the at least one index to a predefined threshold value.

It may be beneficial to terminate the ablation treatment once sufficient treatment results are achieved, such as to prevent exposing the patient to unnecessary treatments. In order to determine the end point of the treatment, i.e. the point in time when the ablation treatment is completed, a threshold value may be determined. The threshold value may then be compared to the value of the at least one index. Hereby, it shall be understood that the threshold value is dependent on the index used. That is, for each individual index, a respective threshold may be selected.

In some embodiments, the apparatus comprises a comparing unit that is adapted to compare the value of the respective index to the thus defined threshold value. The comparing unit may thus derive that the value of the index is below or above the given threshold and, depending on how the threshold has been selected, may indicate that the ablation treatment is complete and may be terminated or has yet to be completed and shall be continued. The corresponding indication may particularly be output to a user, such as a physician, in order to prompt the user to react accordingly.

In some embodiments, the first state corresponds to a state during treatment and the second state corresponds to a reference state. In some embodiments, the reference state is achieved by providing medication to the patient.

Sufficient treatment progression tracking and patient selection may be achieved by means of an index that is indicative between the state of the patient and a corresponding reference state. Hence, in some embodiments, the first state for which the first time series of diagnostic images is acquired corresponds to a patient-specific state of the patient during treatment. In that context, the term during treatment may particularly refer to any stage of the treatment. That is, the patient-specific state may be a state of the patient at the beginning of the treatment, during an ongoing treatment and/or post-treatment. It shall be understood that, for each iteration during which the first time series of diagnostic images is obtained, this patient-specific state may be altered. This is due to the treatment progression. The alteration of the first state during treatment is what allows to track the treatment progress and/or determine the end point of the treatment. Further, by considering a pre-treatment state as a first state, likely responders to the desired ablation treatment may be identified.

The second state may particularly correspond to a reference state. That is, the second time series of diagnostic images indicates a reference. A reference may particularly correspond to a reference to the expected/desired result of the ablation treatment, i.e. should indicate "what the diagnostic images should look like" upon successful treatment. In some embodiments a reference may also correspond to a reference to the initial, sick state, i.e. "what the diagnostic images should no longer look like" upon successful treatment. Other references may be imagined.

In some embodiments, the second time series of diagnostic images indicative of the second, reference state may be derived from clinical studies. In these cases, the second time series may particularly be a pre-stored, patient-unspecific time series from which a second dynamics measure indicative of the reference state may be derived.

In some embodiments, the at least one index is determined as a normalized root mean square error (NRMSE) of the first dynamics measure and the second dynamics measure. In some embodiments, the normalized root mean square error is determined as $$NRMSE = \frac{\sqrt{\sum (DM_{1i} - DM_{2i})^2 / n}}{DM_{max}},$$

wherein $DM_{1i}$ corresponds to the first dynamics measure, $DM_{2i}$ corresponds to the second dynamics measure with i=1, . . . n, and $DM_{max}$ corresponds to the maximum value for a dynamics measure that may be derived for either the first or the second state.

In order to provide an objective comparison, the values of the first and second dynamics measure may be compared by determining a normalized root mean square error (NRMSE) as the at least one index. The NRSME provides a measure of the correspondence between the first dynamics measure and the second dynamics measure. The smaller the NRMSE, the closer the values of the first dynamics measure and the second dynamics measure. Accordingly, the magnitude of the NRMSE may be used as a measure for the completeness/progression of the ablation treatment.

That is, in case the second (reference) state corresponds to a state indicative of the desired outcome of the ablation treatment, a decreasing NRMSE will indicate a continuous (successful) progression of the ablation treatment and a minimal NRMSE will indicate a completed ablation treatment.

On the other hand, in case the second (reference) state corresponds to a state indicative of the initial state of the patient pre-treatment, an increasing NRMSE will indicate a continuous (successful) progression of the ablation treatment and a maximum NRMSE will indicate a completed ablation treatment Thus, in order to determine completion of the ablation treatment, it may be established that NRMSE shall decrease beyond or increase above a particular threshold value.

It shall be mentioned that the NRMSE may also be used as the at least one index when performing appropriate patient selection. Hereby, the NRMSE may particularly be determined for a first state corresponding to a state for the patient prior to the ablation treatment "as is", i.e. a baseline acquisition that is indicative of the microvascular function of the renal arteries for that particular patient without any medication administration and/or ablation treatment having been performed yet. The second (reference) state may hereby correspond to a state that has been derived from a clinical study and is representative of the desired result of the ablation treatment or to a state of a patient who has been administered alpha blocker and thereby being indicative of the effect that the ablation of the nerves around the renal arteries would have for that particular patient. In both cases, the patient may be deemed suitable for the ablation treatment if the determined NRMSE is large.

Going back to the exemplary embodiments for renal denervation described herein above, the NRMSE may exemplary be determined by setting $DM_{1i}$ as the time density curve representing a post-treatment state as the first state and $DM_{2i}$ representing the time density curve representing the reference state as the second state. Further, $DM_{max}$ corresponds to the maximum value of the time density curve of either the first state or the second state. Calculating the NRMSE gives a dynamics index representative of the correspondence between the time density curves. If this index drops below a certain, pre-defined threshold, the ablation is deemed complete.

Hereby, it shall be understood that, due to the specific shape of said curves, the NRMSE may typically have a maximum value of about 0.5. As such, a value of around 0.3 or even 0.2 may still be considered a large value for the NRMSE and, as such, of being indicative of the need to continue with the ablation treatment until the NRMSE becomes even smaller.

Alternatively or additionally, in renal denervation, the NRMSE may be determined by setting $DM_{1i}$ as the time density curve representing the situation post-treatment and $DM_{2i}$ representing the time density curve representing the time density curve post-treatment under the influence of alpha blockers situation. Hereby, $DM_{max}$ again corresponds to the maximum value of the time density curve. In this case also the ablation may be deemed complete, if the NRSME, as the dynamics index, approaches 0.

While in the above examples, the NRSME has been used as the index indicative of the difference between the first and the second state, it shall be understood that, alternatively or additionally, the at least one index may also represent parameters such as time to peak of the perfusion time curve, the upstroke time of the perfusion time curve, peak density or any combination of other time density curve parameters or the like.

In some embodiments, the second time series of diagnostic images may be indicative of the second, reference state may be obtained by administering medication to a patient and, upon medication administration, by acquiring said second time series of diagnostic images. This allows to determine a second dynamics measure indicative of a second, reference state since, by administering the patient with certain medication, such as alpha blockers, a situation in the vasculature is caused in which vasoconstriction is reduced, thereby—again13 providing a reference as to the situation that is aimed to be achieved by the ablation procedure.

In some embodiments, this means that, the patient is injected with the alpha blocker. Hereby, the administration of the alpha blocker may be performed pre-treatment and/or post-treatment. Subsequently, the second time series of diagnostic images is acquired for the patient being under the influence of the just administered medication. The second state that is represented by the thus acquired second time series of diagnostic images is indicative of the desired outcome of the ablation treatment.

In some embodiments, the first time series of diagnostic images of the region of interest may be acquired for the patient post-treatment without medication.

The first and second dynamics measure is then derived from the first and second time series of diagnostic images, respectively, and, based on the first and second dynamics measure, a respective index is determined. This index may then be compared to a threshold value in order to determine whether or not the ablation treatment has reached its end point. Hereby, a completed ablation may be recognized by the fact that there is no (significant) difference in the second dynamics measure representing the situation where vasoconstriction is suppressed by means of the alpha blocker and the first dynamics measure representing the situation without such suppression.

In some embodiments, the first time series of diagnostic images of the region of interest may also be acquired for the patient pre-treatment without medication.

In this case also, the first and second dynamics measure may then be from the first and second time series of diagnostic images, respectively to determine a respective index. This index may then be evaluated to determine whether or not the patient is suitable for a successful ablation treatment. Typically, if the patient is susceptible to the treatment, the deviation between the pre-treatment state without medication and the state with medication will be large, thereby resulting in a large index (such as the NRMSE). In some embodiments, the thus determined index may then be compared to an index-such as the NRMSE-derived from a clinical study, said index from the clinical study being indicative of a pre-treatment index for a patient who has successfully been treated using renal denervation. This could give a guideline to the user, such as the physician, such as to determine if the patient regarded is suitable for the denervation treatment or not.

For the specific case of renal denervation, this approach may particularly encompass administering the alpha blocker intra-renally, thereby blocking the sympathetic nerves and collecting the second time series of diagnostic images of the region of interest on the kidney pre- and/or post-treatment for the medicated patient. Further, the first time series of diagnostic images of the region of interest on the kidney may be acquired post-treatment. The index representing indicative of the difference between the first state and the second state (and, hence, indicative of the progression of the renal denervation process) may then be determined by comparing, as the second dynamics measure, the perfusion time curve obtained for the patient under medication and, as the first dynamics measure, the perfusion time curve obtained for the patient without medication, but after the ablation treatment. The denervation is hereby deemed completed if the change between the first and the second dynamics measure (i.e. between both perfusion time curves) is minimal.

In some embodiments, the region of interest is subdivided into a first sub-region of interest and a second sub-region of interest, wherein the first time series of diagnostic images is obtained for the first sub-region of interest for the first state and the second time series of diagnostic images is obtained for the first sub-region of interest for the second state, and a third time series of diagnostic images is obtained for the second sub-region of interest for the first state, and a fourth time series of diagnostic images is obtained for the second sub-region of interest for the second state, wherein the processing unit is further adapted to derive, from the first time series of diagnostic images, a first dynamics measure indicative of a contrast agent dynamic through the first sub-region of interest over time for the first state, derive, from the second time series of diagnostic images, a second dynamics measure indicative of a contrast agent dynamic through the first sub-region of interest over time for the second state, derive, from the third time series of diagnostic images, a first dynamics measure indicative of a contrast agent dynamic through the second sub-region of interest over time for the first state, derive, from the fourth time series of diagnostic images, a second dynamics measure indicative of a contrast agent dynamic through the second sub-region of interest over time for the second state, and determine, the at least one index indicative of a relative difference between the first state and the second state based on the first dynamics measures and the second dynamics measures.

In some embodiments, the at least one index indicative of the difference between the first state and the second state may by derived by determining a dynamics measure at different locations of the region of interest. For that purpose, the region of interest may be subdivided into a first sub-region and a second sub-region. A first time series of diagnostic images may be acquired for the first sub-region for the first state and a third time series of diagnostic images may be acquired for the second sub-region, in the first state. It shall be understood that the first and the third time series may correspond to one time series acquired at one particular time, whereby the diagnostic images of the one time series are then sub-divided according to the sub-division of the region of interest. That is, the first time series corresponds to the first sub-region and the third time series corresponds to the second sub-region. In some embodiments, the first state may correspond to a post-treatment state.

Further, a second time series of diagnostic images may be acquired for the first region in the second state and a fourth time series of diagnostic images may be acquired for the second sub-region for the second state. Here, it shall be understood that the second and the fourth time series may also correspond to one time series acquired at one particular time, whereby the diagnostic images of the one time series are then sub-divided according to the sub-division of the region of interest. That is, the first time series corresponds to the first sub-region and the fourth time series corresponds to the second sub-region. In some embodiments, the second state may particularly correspond to a pre-treatment state of the patient and the first state may correspond to a post-treatment state of the patient.

The first and third time series of diagnostic images may then each be analyzed to derive a first dynamics measure for the first state in the first sub-region and the second sub-region, respectively. The second and fourth time series of diagnostic images may each be analyzed to derive a second dynamics measure for the second state in the first sub-region and the second sub-region, respectively.

The thus determined first and second dynamics measures (for the first and the second sub-region) may then be used to determine an index indicative of the difference between the first state and the second state. For this purpose, the first dynamics measure derived for the first sub-region and the first dynamics parameter derived for the second sub-region may be used to determine a state 1 index. The second dynamics measure for the first sub-region and the second sub-region may be used to determine a state 2 index. Hereby, due to the second state corresponding to a pre-treatment state, the state 2 index is indicative of the patient's state pre-treatment. Equally, due to the first state corresponding to a post-treatment state, the state 1 index is indicative of the dynamics situation post-treatment. The at least one index indicative of the difference between the first state and the second state may then be determined as the difference between the state 2 index and the state 1 index.

In some embodiments, the state 2 index may particularly correspond to a pre-treatment NRSME(pre) determined for the first sub-region and the second sub-region respectively, using the first dynamics measure of the first sub-region and the first dynamics measure of the second sub-region. Further, the state 1 index may particularly correspond to a post-treatment NRSME(post) determined for the first sub-region and the second sub-region using the second dynamics measure of the first sub-region and the second dynamics measure of the second sub-region.

Subsequently, the at least one index indicative of the difference between the first state and the second state may particularly be determined according to NRSME=NRSME(pre)−NRSME(post).

Again, in this case as well, the NRSME may be compared to a predefined threshold value, whereby the treatment is deemed completed if the NRSME drops below said predefined threshold.

In some embodiments, the at least one index may again specifically be employed to provide treatment guidance for renal denervation. In this case, the first dynamics measure for the first sub-region may correspond to a time intensity curve of the renal cortex as the first region and the first dynamics measure for the second sub-region may correspond to a time intensity curve of the renal medulla as the second region. The first dynamics measure may be indicative of the first state, which is a post-treatment state.

Likewise, the second dynamics measure for the first sub-region may correspond to a time intensity curve of the renal cortex and the second dynamics measure for the second sub-region may correspond to the time intensity curve of the renal medulla. The second dynamics measure may be indicative of the second state, which is a pre-treatment state. Since the sympathetic nervous system mainly impacts renal perfusion of the cortex, a successful ablation treatment in this case can be determined by considering the change in tissue intensity curve of the medulla and the renal cortex compared to a baseline RDN, i.e. a measurement performed prior to the ablation treatment.

In some embodiments, the first time series and/or the second time series are acquired using one or more predetermined acquisition settings.

It may be beneficial to improve reproducibility of the method for providing treatment guidance. One possibility to achieve this is by standardizing the used intensity by obtaining the first and/or second time series of diagnostic images using a plurality of predetermined acquisition settings. In some embodiments, these predetermined acquisition settings may particularly relate to contrast agent concentration, contrast agent injection rate, speed, pressure or the like. By having these settings predetermined, it is possible to standardize the first and second dynamics measure and, as such, the possible perfusion parameters derived therefrom in case the diagnostic images of the first and second time series correspond to X-ray perfusion images.

In some embodiments the input unit is further adapted to receive additional patient data, and wherein the processing unit is adapted to determine the at least one index at least partially based also on the additional patient data.

In some embodiments, the information derived from the first and second time series and/or the third and fourth time series may be combined with additional current or previously collected patient data such as blood pressure, body temperature, blood oxygenation, hematocrit, Glomular Filtration rate, creatine level, drug specifics, such as dose, concentration, administration and further patient specifics such as age, gender, etc. Since all these factors influence the sympathetic renal nerve activity, this additional information may help improving accuracy of the treatment guidance.

In some embodiments, the processing unit is further adapted to derive the first dynamics measure for the first state and/the second dynamics measure for the second state by: deriving, for each point in time, a value for the first dynamics measure and/or the second dynamics measure, representing the values for the first dynamics measure and/or the second dynamics measure as a function of time.

In some embodiments, the first dynamics measure and the second dynamics measure correspond to time-dependent curves of a measurement value that may be derived from the first and second time series of diagnostic images. That is, the first dynamics measure may correspond to a first time-dependent curve, such as a time intensity curve, for the first state and the second dynamics measure may correspond to a second time-dependent curve, such as a time intensity curve, for the second state. These curves may be plotted by deriving, for each of the diagnostic images in the time series—or a subset thereof—a particular value plotted as a function of measurement time, whereby the measurement time indicates the point in time where the respective diagnostic image was acquired. In some embodiments, the particular value may correspond to the intensity value indicating the intensity of the contrast agent through the vasculature in the region of interest. In other embodiments, the value may correspond to the relative intensity of the contrast agent-filled vessels compared to the entirety of the region of interest. Further values may be imagined.

In some embodiments, the determining of the at least one index comprises analyzing, based on the first dynamics measure and the second dynamics measure, one or more of the following for the first state and the second state, respectively:

an arrival time of the contrast agent;
a wash in rate of the contrast agent,
a wash out rate of the contrast agent
a time to peak of the first and/or second dynamics measure,
a duration of peak of the first and/or second dynamics measure,
a peak value of the first and/or second dynamics measure,
an average peak value of the first and/or second dynamics measure, and/or
an area under a curve representing the values for the first dynamics measure and/or the second dynamics measure as a function of time.

In some embodiments, individual parameters may be analyzed to provide treatment guidance. These parameters may particularly relate to the arrival time, the wash in rate, the wash out rate, the time to peak, the duration of the peak, the peak value, the average peak value and/or the area under a curve, such as a time intensity curve or a perfusion time curve.

Any of these parameters or a linear combination thereof may be used for assessment of the completeness of the ablation treatment. Hereby, these parameters may be measured all at once or during differently selected time intervals.

In order to determine the relative difference between the first state and the second state, respectively, i.e. to compare the first and the second state, an index according to $$idx = \frac{V_1}{V_2},$$

whereby $V_1$ corresponds to a value for one of the parameters that may be used to provide treatment guidance in the first state and $V_2$ corresponds to a value for the same parameter in the second state.

It shall be understood that, although some specific implementations of the invention have been outlined herein above, the invention is not limited thereto. In particular, it is possible to use different indices as an indication for the difference between the first state and the second state. One possible index is the normalized root mean square error (NRMSE) as discussed herein above. Further, the relative differences between the first and the second state may be compared using cross-correlation or a Kolmogorov-Smirnoff test.

In the most general manner, an index indicative of the relative difference between the first state and the second state may be defined as $$idx = \frac{(aV_1 + bV_2)}{(cV_1 + dV_2)},$$

whereby $V_1$ corresponds to a value for one of the parameters in the first state and $V_2$ corresponds to a value for the same parameter in the second state and a,b,c and d correspond to variables which may be chosen in accordance with the parameter selected for determination of the index. By using this generalized formula, it is possible to determine indices such as $$idx = \frac{V_1}{V_2},$$

but also indices which are indicative of the difference of the respective parameter value divided by an average parameter value, namely by choosing the variables a,b,c and d as $$a = 1, b = -1, c = d = 0.5.$$

In some embodiments, the output unit comprises an indication unit adapted to generate a visual, auditory, haptic and/or audiovisual indication that the ablation treatment is complete, and to output said indication to the user.

According to some embodiments, the apparatus is further provided with an indication unit, such as a loud speaker and/or a display and/or a vibration device that allows the apparatus to provide a recognizable output to the user if it is determined that the ablation treatment has been completed. That is, if the apparatus, upon comparing the at least one dynamics index to the predefined threshold, determines that the ablation treatment has been successfully completed, the indication unit may output the indication that this is the case such as to prompt the user to terminate the procedure. By means of this arrangement, unnecessarily long treatment procedures may be avoided.

According to a further aspect, a method for providing treatment guidance for an ablation treatment, comprising the steps of: receiving a first time series of diagnostic images of a region of interest of a patient's vasculature, the first time series representing a first state, receiving a second time series of diagnostic images of the region of interest of the patient's vasculature, the second time series representing a second state, deriving, from the first time series of diagnostic images, at least one first dynamics measure indicative of a contrast agent dynamic through the region of interest over time for the first state, deriving, from the second time series of diagnostic images, at least one second dynamics measure indicative of a contrast agent dynamic through the region of interest over time for the second state, determining, based on the at least one first dynamics measure and the at least one second dynamics measure, at least one index indicative of a relative difference between the first state and the second state and outputting the at least one index to a user.

The method may be a computer implemented method. The input may be part of a controller or a processing unit. The controller or processing unit may be part of the computer and or the apparatus.

In an even further aspect, a computer program for controlling an apparatus according to the invention is provided, which, when executed by a processing unit, is adapted to perform the method steps according to the invention. According to yet another aspect, a computer-readable medium having stored thereon the computer program is provided.

It shall be understood that the apparatus, the method, the computer program, and the computer-readable medium as claimed, have similar and/or identical preferred embodiments, in particular, as defined in the dependent claims. It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
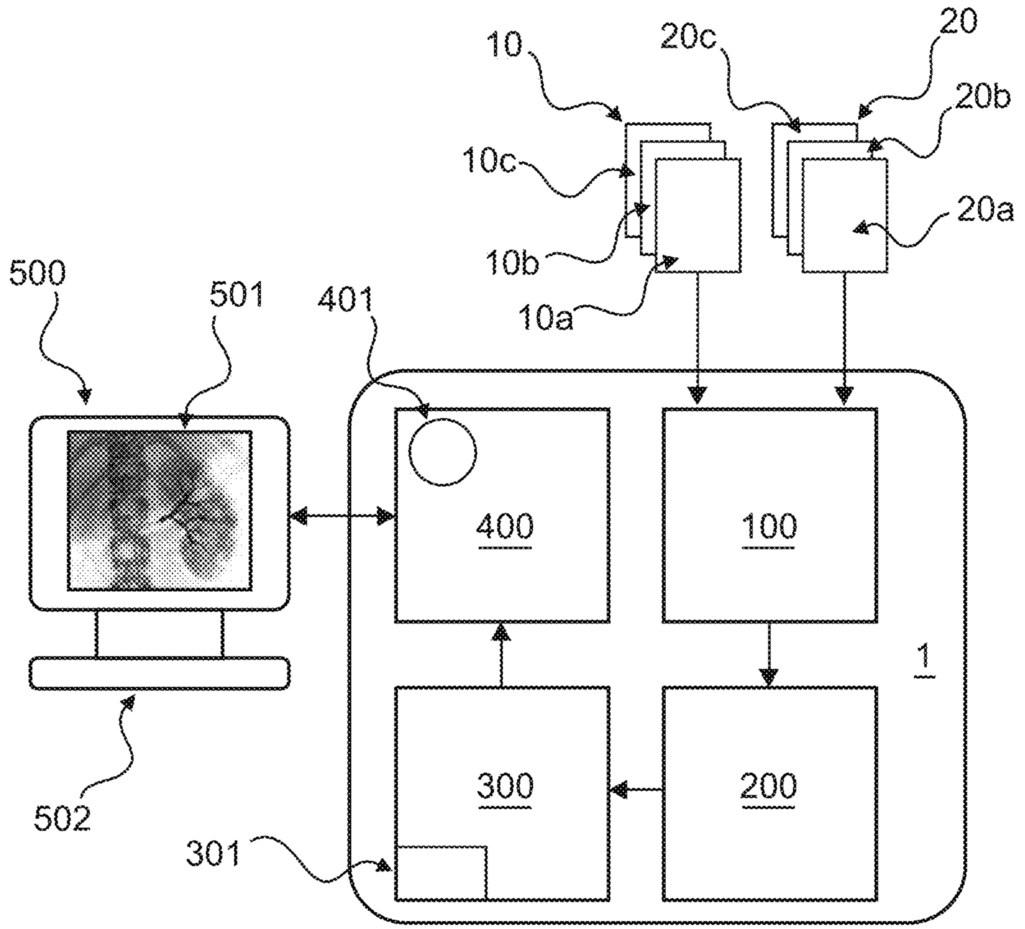
FIG. 1 schematically illustrates an apparatus for providing treatment guidance for an ablation treatment according to a first embodiment.

The illustration in the drawings is schematically. In different drawings, similar or identical elements are provided with the same reference numerals.

FIG. 1 represents schematically an exemplary embodiment of an apparatus 1 for providing treatment guidance for an ablation treatment. In the exemplary embodiment of FIG. 1, the ablation treatment is performed for the purpose of renal denervation. That is, the ablation treatment is performed on the vessel wall of the renal artery.

The apparatus 1 comprises an input unit 100, a processing unit 200, a comparing unit 300 and an output unit 400. The output unit 400 comprises an indication unit 401 and is communicatively coupled to user interface 500, including a display unit 501 and an input unit 502.

The input unit 100 receives a first time series 10 of diagnostic images representing a first state and a second time series 20 of diagnostic images representing a second state. In the exemplary embodiment according to FIG. 1, the first time series 10 of diagnostic images comprises a plurality of X-ray perfusion images 10*a*, 10*b*, 10*c* which have been acquired for a region of interest on the patient's kidney after a renal denervation treatment. That is, the first state corresponds to a post-treatment state specific to the patient.

The second time series 20 of diagnostic images comprises a plurality of X-ray perfusion images 20*a*, 20*b*, 20*c* which represent a second, reference state for the same region of interest on the patient's kidney. In order to represent an appropriate reference, the plurality of X-ray perfusion images 20*a*, 20*b*, 20*c* may be obtained from a clinical study or may correspond to a time series 20 of diagnostic images that has been acquired for a medication-induced reference state. Such a medication-induced reference state may be achieved by administering an alpha blocker, such as Tolazoline or Phentolamine, intra-renally to the patient. The alpha blocker causes the alpha receptors causing vasoconstriction to be blocked, i.e. results in a blocking of the sympathetic nerves in the renal artery, thereby rendering the renal artery into a state in which the microvascular impedance is reduced. Upon administration, the second time series 20 of diagnostic images may then be acquired.

In some embodiments, the reference state may also correspond to a pre-treatment state determined for a particular patient. That is, in some embodiments, the second time series 20 of diagnostic images may have been acquired for the particular patient pre-treatment. This allows to derive the initial state of the patient prior to the ablation treatment and, as such, also allows to determine, based on a further (e.g. during- or post-treatment) the progression of the ablation treatment.

Upon receipt at the input unit 100, the first time series 10 and the second time series 20 are provided to the processing unit 200. The processing unit 200 derives, from the first time series 10 of diagnostic images, a first dynamics measure indicative of the contrast agent dynamic through the region of interest over time in the first, post-treatment state and, from the second time series 20 of diagnostic images, a second dynamics measure indicative of the contrast agent dynamic through the region of interest over time in the second, reference state.

Figure 2:
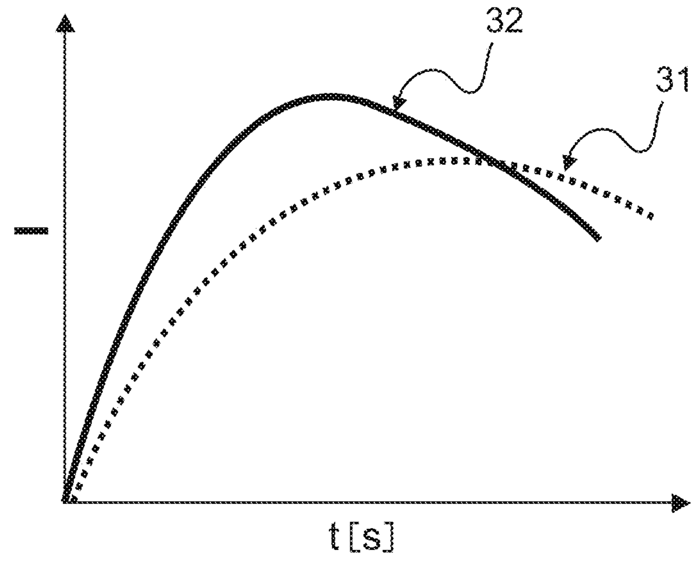
FIG. 2 shows a first dynamics measure indicative of a first state and a second dynamics measure indicative of a second state according to the embodiment.

In the specific embodiment according to FIG. 1, the region of interest is on the kidney. FIG. 2 schematically represents the first dynamics measure and the second dynamics measure derived by the apparatus 1 according to the embodiment of FIG. 1. Hereby, the first dynamics measure corresponds to a time intensity curve 31 for the renal artery after renal denervation, i.e. in the post-treatment state. The second dynamics measure corresponds to a time intensity curve 32 for the renal artery in case of a reference state, i.e. a reference for a successful renal denervation treatment.

The processor 200 then uses the first dynamics measure and the second dynamics measure to determine at least one index indicative of relative difference between the time intensity curve 31, representing the first state and the time intensity curve 32, representing the second state. This index is indicative of the progression (and success) of the ablation treatment.

In the exemplary embodiment according to FIG. 1, this means that the processor 200 determines a normalized root mean square error (NRMSE) between the perfusion in the first, post-treatment state and the perfusion in the second, reference state. Thus, processor 200 derives a quantitative measure of the similarity between both perfusion curves according to $$NRMSE = \frac{\sqrt{\sum (DM_{1i} - DM_{2i})^2 / n}}{DM_{max}},$$

wherein $DM_{1i}$ corresponds to the perfusion curve in the region of interest for the first state and $DM_{2i}$ corresponds to the perfusion curve in the region of interest for the second state, whereby i=1, . . . n. $DM_{max}$ corresponds to the maximum value for the perfusion curve in the region of interest.

The processing unit 200 determines the index NRMSE and provides the index to the comparing unit 300. The comparing unit 300 derives a predefined threshold value for the index and compares the received index to said derived threshold value. In the exemplary embodiment of FIG. 1, the comparing unit 300 comprises a memory 301, in which the threshold value is stored and derives the threshold value by reading it from the memory 301. Hereby, the comparing unit 300 determines that the renal denervation has been (successfully) completed if the comparison to the threshold value shows that the index is below said predefined threshold value, in particular below 0,1, more preferable below 0,05. In the exemplary embodiment of FIG. 1, a threshold value that indicates completed renal denervation is indeed approaching 0, 0, since the medication-induced reference state corresponds to a successful ablation.

The comparing unit 300 is then configured to provide the index, optionally along with the comparison result, to the output unit 400. The output unit 400 is configured to output the index to a user. In the specific embodiment according to FIG. 1, this means that the output unit 400 provides the index to user interface 500 comprising display unit 501 and input unit 502. The display unit 501 may be configured to generate a graphical representation of the index and display it, optionally along with at least one diagnostic image of the region of interest, to the user.

In the specific embodiment according to FIG. 1, output unit 400 comprises an indication unit 401. If the comparison result is provided to output unit 400 and if the comparison result indicates that renal denervation has been completed, indication unit 401 may generate an (additional) indication that the renal denervation is completed and provide said indication to the user. In the exemplary embodiment, this indication is an auditory indication and indication unit 401 output this auditory indication. It shall be understood, though, that the indication may also be a visual, haptic or audiovisual indication and that indication unit 401 may output this indication directly or through user interface 500, in particular display unit 501.

Upon receipt of the completion indication, the user, typically a physician, may be prompted to terminate the renal denervation procedure or, if the procedure is already terminated, receive a confirmation that the procedure was successful.

Figure 3:
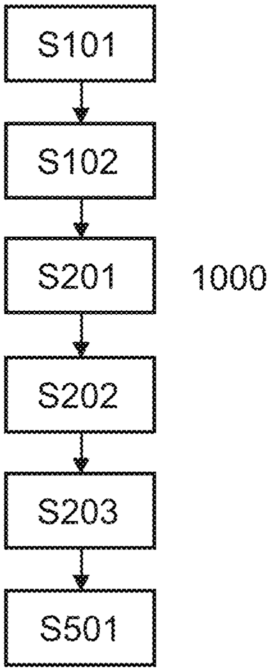
FIG. 3 illustrates an exemplary method for providing treatment guidance for an ablation treatment according to a first embodiment.

FIG. 3 schematically represents an exemplary embodiment of a method 1000 for providing treatment guidance for an ablation treatment, in particular a renal denervation treatment, according to a first embodiment. In accordance with this first embodiment, the method 1000 for providing treatment guidance is used to identify likely responders to a renal denervation treatment, as may exemplary be implemented by apparatus 1 according to FIG. 1.

The method starts at step S101, where a first time series 10 of diagnostic images is received, whereby the first time series 10 of diagnostic images represents a first state. In the specific embodiment according to FIG. 3 where the method 1000 is used to identify likely responders to the treatment, the first state corresponds to a pre-treatment state for the patient to be considered, i.e. for a patient suspected of sympathetic overdrive.

In step S102, a second time series 20 of diagnostic images representing a second state is received. In the embodiment according to FIG. 3, the second state corresponds to a reference state, i.e. represents a non-sympathetic overdrive condition. In the specific embodiment according to FIG. 3, the second time series 20 of diagnostic images is hereby obtained from a clinical study and derived from a storage for further evaluation. Although, in the embodiment according to FIG. 3, the reference state is derived from a clinical study, it may be understood that, alternatively or additionally, the reference state may likewise be obtained by administering an alpha blocker intra-renally to the patient and subsequently performing an actual X-ray perfusion measurement for the patient under medication. Other methods for obtaining a second time series 20 representing a reference state may also be considered. What is decisive for the reference state is that it represents the state that could be achieved upon successful renal denervation.

In step S201, a first dynamics measure is derived from the first time series 10 of diagnostic images, the first dynamics measure indicative of the contrast agent dynamic through the region of interest over time in the first, pre-treatment state. In the specific embodiment according to FIG. 3, this first dynamics measure corresponds to a time intensity curve for the renal vasculature and/or renal artery for the particular patient suspected of sympathetic overdrive and, thus, considered for renal denervation.

In step S202, a second dynamics measure is derived from the second time series 20 of diagnostic images, the second dynamics measure indicative of the contrast agent dynamic through the region of interest over time in the second, reference state. This second dynamics measure also corresponds to a time intensity curve for the renal vasculature and/or renal artery, whereby this time intensity curve is derived from clinical studies and, therefore, representative of a non-sympathetic overdrive condition.

In step S203, at least one index indicative of relative difference between the first state and the second state is determined. In the exemplary embodiment according to FIG. 3, a normalized root mean square error (NRMSE) between the first time intensity curve and the second time intensity curve is determined in step S203. The index NRMSE is then provided to be output, in particular presented to the user in step S501. Based on this index, the user may then determine whether or not the patient is a likely responder for a renal denervation treatment. Optionally, the display of the index in step S501 may hereby be accompanied by the presenting of a treatment recommendation. In this case, the apparatus may already determine, optionally based on a comparison of the determined index to a pre-determined threshold value, whether the patient is a likely responder or not and may output this indication, in addition to the index, to the user.

Figure 4:
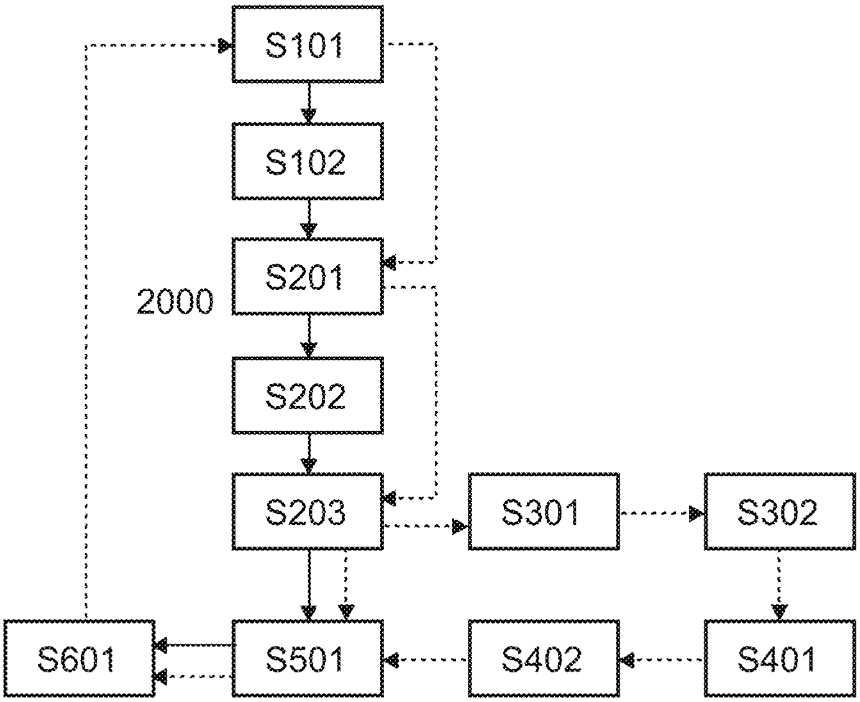
FIG. 4 illustrates an exemplary method for providing treatment guidance for an ablation treatment according to a second embodiment.

FIG. 4 schematically represents an exemplary embodiment of a method 2000 for providing treatment guidance for an ablation treatment, in particular a renal denervation treatment, according to a second embodiment. In accordance with this second embodiment, the method 2000 for providing treatment guidance is used to perform monitoring of the treatment progress during an ablation treatment, in particular for the purpose of renal denervation. The method 2000 for monitoring the treatment progress may also be implemented by apparatus 1 according to FIG. 1.

Steps S101 and S102 are performed in a similar manner as explained with respect to the first embodiment according to FIG. 3. That is, in step S101, a first time series 10 of diagnostic images is received, whereby the first time series 10 of diagnostic images represents a first state. In the exemplary embodiment according to FIG. 4, this first state corresponds to the current state of the patient during the ongoing ablation treatment. That is, when the method 2000 is initialized for the first time, the first time series 10 of diagnostic images may particularly correspond to a pre-treatment state for the patient, i.e. a state of the patient prior to the ablation treatment to be monitored.

Further, in step S102, a second time series 20 of diagnostic images representing a second state is received. Hereby, the second time series 20 of diagnostic images may have been obtained as described in relation to the first embodiment according to FIG. 3. Further, steps S201, S202 and S203 are performed as described in relation to FIG. 3 prior to the start of the ablation treatment. That is, the first dynamics measure is determined from the first time series 10 and the second dynamics measure is determined from the second time series 20 and the first and second dynamics measure are used to determine at least one index indicative of relative difference between the first state and the second state. is determined. This index may be presented to the user, optionally along with a treatment recommendation, in step S501.

In step S601, the ablation treatment is then started. After some time has passed, steps S101, S201, S203 and S501 are repeated. The repeated steps are marked by the dotted lines in FIG. 4.

That is, in step S101, a further first time series 10 of diagnostic images is obtained, representing the first, current state of the patient. During repetition after some time from the start of the ablation treatment, the current state of the patient should have changed if the patient responds to the ablation treatment. Accordingly, the index calculated in step S203 also changes. The change of the index may be presented in step S501.

Optionally, the method 2000 for providing ablation monitoring may also include steps S301 to S402. In step S301, a predefined threshold value for the index is derived. Subsequently, in step S302, the index derived in step S203 for the current state of the patient is compared to the predefined threshold value and a respective comparison result is generated. In step S401, the comparison result may be evaluated by a respective processor. In some embodiments, the evaluation may be performed by the processing unit 200 and/or the comparing unit 300 and/or the output unit 400 of the apparatus 1 according to FIG. 1. In some embodiments, a dedicated evaluation unit may be provided for that purpose. Based on the evaluation of the comparison result, it may be determined whether or not the ablation treatment, i.e. the renal denervation treatment has been completed. This determination may particularly be based on whether or not the comparison result indicates that the index calculated in step S203 is below the predetermined threshold value. If this is the case, the treatment is deemed completed. If it is not, the treatment is continued.

In step S402, a respective indication of the evaluation of the comparison result is generated and, optionally, displayed to the user in step S501. In some embodiments, further indications may be output to the user such as to prompt the user to stop the treatment if it is deemed completed. In some embodiments, the indication may also be used to signal to the treatment device used for the ablation treatment to automatically terminate the treatment if it is deemed completed.

In the exemplary embodiment according to FIG. 4, steps S101, S201, S203 and S301 to S601 are repeated until it is determined that the ablation treatment has been finalized and/or that the patient does not respond to the ablation treatment. This allows to frequently monitor the treatment progress.

Figure 5:
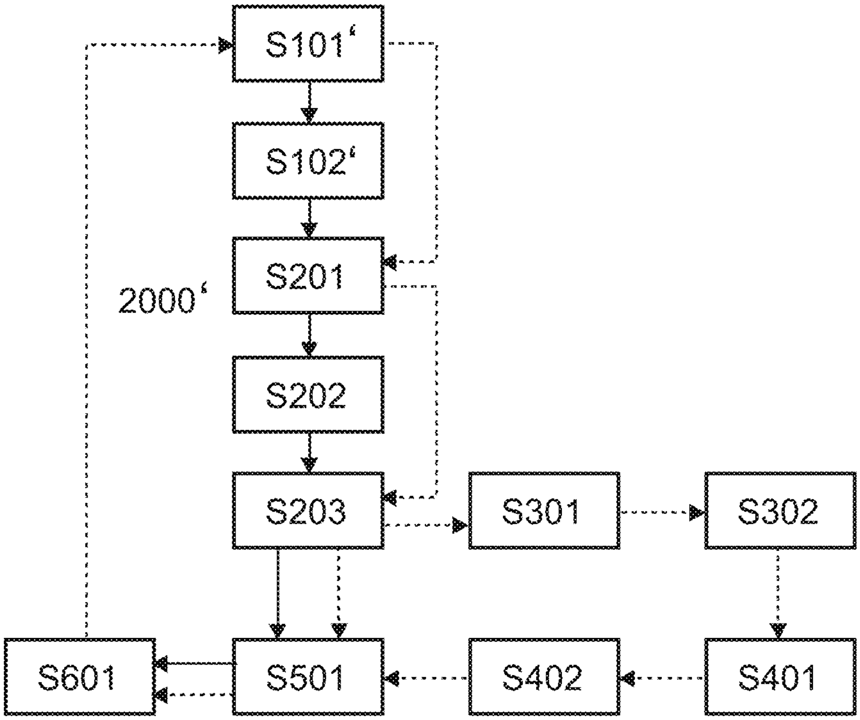
FIG. 5 illustrates an exemplary method for providing treatment guidance for an ablation treatment according to a modification of the second embodiment.

FIG. 5 illustrates a modification 2000' of the method 2000 according to FIG. 4. That is, the method 2000' is likewise used for performing treatment monitoring during the ablation treatment. In general, the monitoring is performed in a similar manner as the monitoring according to the embodiment of FIG. 4. To avoid repetitions, only the differences between the embodiment according to FIG. 4 and the modification according to FIG. 5 will be described.

In steps S101' and S102', again a first time series 10 of diagnostic images representative of a first state and a second time series 20 of diagnostic images representative of a second state are obtained, respectively. Hereby, the first and the second time series are both acquired from the patient suspected of sympathetic overdrive. The second time series 20 representative of the second, reference state is hereby obtained for the patient prior to the ablation treatment and the first time series 10 representative of the first, current state is obtained after some time after the ablation treatment has started. That is, the first time series 10 is representative of the patient's state during the ablation treatment, whereas the second time series 20 is representative of the patient's state prior to the ablation treatment, whereby this state prior to the ablation treatment is considered the reference state.

In steps S201 and S202, the respective first and second dynamics measures are obtained and used for index calculation in step S203 as described herein above in relation to FIG. 4. In step S501 the thus determined index is displayed in the known manner. The process as repeated as described in relation to FIG. 4. In particular, the comparison of the index to a predetermined threshold and the output of a respective indication is performed as previously described in order to track the treatment progress. Hereby, it shall be mentioned that, due to the index according to FIG. 5 being a different one, namely being a patient-specific index indicative of the relative difference between the pre-treatment state of the patient and the current (during-treatment) state of the patient, the threshold value derived in step S301 is also a different one compared to the threshold value used in FIG. 4. That is, the threshold value that is used to determine when the treatment has been completed has to be chosen for each index specifically.

In some embodiments, the treatment monitoring may also be performed using medication administration, in particular alpha blocker administration in order to obtain a reference. That is, in such an embodiment, the user, i.e. the physician, may—based on experience or based on a certain time frame—consider the ablation treatment to be completed. Upon (considered) completion of the ablation treatment, the physician may then opt for administering an alpha blocker intra-renally to the patient and may then collect a second time series 10 of diagnostic images, such as an X-ray perfusion time series, for the patient as a reference state. From this second time series 10, a second dynamics measure may be determined in the known manner. Further, a first time series 10 of diagnostic images may be obtained for the patient after the (considered) completion of the ablation treatment without any alpha blocker. From this first time series 10, the first dynamics measure may be derived. The first and second dynamics measure may then be used to calculate the index in the known manner. Completion of the ablation treatment may be assumed if the index indicates a minimal or non-existent relative difference between the first state and the second state.

In some modification of the above-defined embodiments, additional measurement data, in particular additional parameters relevant for renal denervation may be considered to determine an appropriate reference state and/or to perform a more accurate evaluation of the treatment progress. In that context, particularly beneficial measurement data may for example comprise measurements such as blood pressure (systolic, diastolic, taken at different locations of the patient's body, etc.), body temperature, blood oxygenation, hematrocryt, Glomular Filtration rate, creatine level, drug specifics such as dose, concentration, administration or other patient specifics such as age, gender or the like. All these parameters allow to draw conclusions with respect to the achieved sympathetic renal nerve activity remaining, the reduction, the increase, the specific renal filtration, the perfusion in the renal area and/or the left and/or right renal activity, thereby increasing the accuracy of the determination of the reference state and/or the evaluation.

Figure 6A:
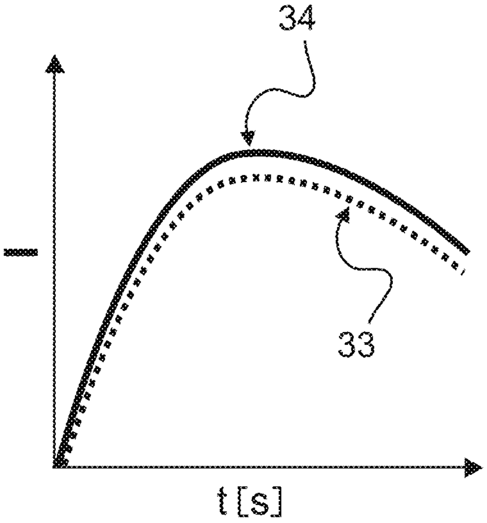
FIG. 6A illustrates a set of time series curves as obtained for two sub-regions of the region of interest in the first state.
Figure 6B:
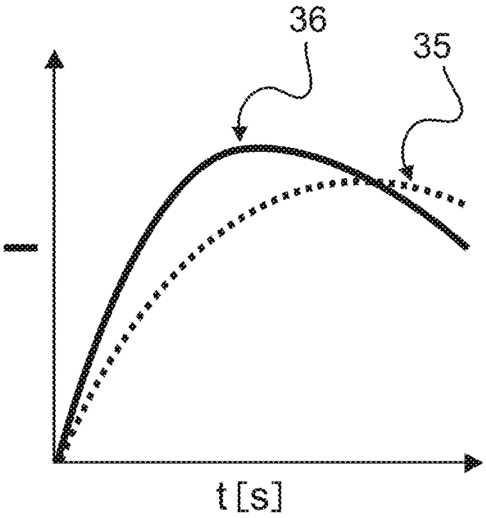
FIG. 6B illustrates a set of time series curves as obtained for two sub-regions of the region of interest in the second state.

FIG. 6A and FIG. 6B schematically illustrate two sets of time intensity curves used as respective dynamics measures according to a further embodiment. In the embodiment according to FIGS. 6A and 6B, the ablation treatment is performed for the purpose of renal denervation. As such, the region is of interest corresponds to the kidney. Hereby, the region of interest has been subdivided into a first sub-region of interest and a second sub-region of interest. In the specific embodiment according to FIGS. 6A and 6B, the first sub-region of interest corresponds to the renal cortex and the second sub-region of interest corresponds to the renal medulla.

FIG. 6A hereby illustrates a time intensity curve 33 for the first sub-region, i.e. the renal cortex, whereby the time intensity curve 33 has been derived from the first time series 10 obtained for the first sub-region of interest in a first state in the manner as described in relation to FIG. 1. Further, FIG. 6A illustrates a time intensity curve 34 for the second sub-region, i.e. the renal medulla which has been derived from a third time series obtained for the second sub-region of interest in the first state. In the specific embodiment according to FIG. 6A, the first state hereby particularly corresponds to a post-treatment state, i.e. a state of the renal cortex and renal medulla after renal denervation treatment.

FIG. 6B illustrates a time intensity curve 35 for the first sub-region which has been derived from the second time series 20 obtained for the first sub-region of interest in a second state and a time intensity curve 36 for the second-sub-region which has been derived from a fourth time series of diagnostic images obtained for the second sub-region of interest in the second state. In the specific embodiment according to FIG. 6B, this second state corresponds to a pre-treatment state, i.e. a state of the renal cortex and the renal medulla prior to the renal denervation treatment.

In the specific embodiment according to FIGS. 6A and 6B, the index is determined by comparing the time intensity curves 33 and 34 for the first state and the time intensity curves 35 and 36 for the second state. Since the sympathetic nervous system mainly impacts renal perfusion of the cortex, a successful ablation may be determined by the change in the time intensity curve of the medulla and the renal cortex compared to a baseline measurement prior to an ablation treatment for renal denervation, e.g. by determining the normalized root mean square error or by considering a change in a particular parameter describing the effect of renal denervation on the renal cortex and renal medulla. In this case, one possible index indicative of the relative difference between the first state and the second state may e.g. be determined as $$idx = \frac{(V_{1,reg1} - V_{1,reg2})}{(V_{2,reg2} - V_{2,reg1})},$$

whereby $V_{1,reg1}$ is a parameter (such as a value representing the time intensity curve) for the first sub-region in the first state, $V_{1,reg2}$ is a parameter for the second sub-region in the first state, $V_{2,reg1}$ is a parameter for the first sub-region in the second state and $V_{2,reg2}$ is a parameter for the second sub-region in the second state.

Another possible index that may be used in this case is the comparison of the normalized root mean square error as determined for both regions relative to a baseline RDN for the first and second state respectively, according to $$idx = \frac{NRSME(reg_1, reg_2)_{state1}}{NRSME(reg_1, reg_2)_{state2}},$$

whereby the NRSME for both states may be calculated according to $$NRMSE = \frac{\sqrt{\sum (TIC_{1i} - TIC_{2i})^2 / n}}{TIC_{max}},$$

wherein $TIC_{1i}$ corresponds to the time intensity curve for the first time series in both states and $TIC_{2i}$ corresponds to the time intensity curve for the second time series in both states. Hereby, i=1, . . . n, and $TIC_{max}$ corresponds to the maximum value for a time intensity curve that may be derived.

Although in the above-cited embodiments, the diagnostic images have been acquired using X-ray perfusion angiography for tracking the contrast agent, it shall be understood that other imaging modalities and other fluids may likewise be used, as long as the imaging modality and the fluid are each selected such that the fluid through the vasculature may be traced using the imaging modality.

Further, it shall be understood that, while the X-ray imaging has been performed at a single energy, dual energy X-ray measurements may also be used for quantifying the dynamics measure, as these measurements allow to more accurately quantify the iodine concentration in the contrast agent. Further, background subtraction may be enabled which removes overlaying and disturbing anatomy.

Further, while in the above-cited embodiments, the treatment guidance is described in relation to renal denervation, it shall be understood that the treatment guidance process may likewise be adapted to other ablation-based treatments which rely on the change of fluid flow dynamics as a result of the ablation process.

While in the above-cited embodiments the normalized root mean square error (NRMSE) has been used as the at least one dynamics index, it shall be understood that other indices may likewise be used, as long as they are indicative for the relation between the first and the second dynamics measure.

Further, while in the above-cited embodiments, the apparatus itself derives the first and second dynamics measure from the first and second time series, it shall be understood that the term deriving is to be interpreted broadly and may also encompass the importing of the first dynamics measure and/or the second dynamics measure from other measurement modalities to determine the dynamics index.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the deriving of the first and/or the second dynamics measure, the determining of the at least one index indicative of the relative difference between the first and the second state, the comparing of the at least one index to a predefined threshold value, the generating of the indication that the ablation treatment is complete et cetera performed by one or several units or devices can be performed by any other number of units or devices. These procedures in accordance with the invention can hereby be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to an apparatus for providing treatment guidance for an ablation treatment, comprising an input unit adapted to receive a first time series of diagnostic images of a region of interest of a patient's vasculature, the first time series representing a first state and a second time series of diagnostic images of the region of interest of the patient's vasculature, the second time series representing a second state, a processing unit adapted to derive, from the first time series of diagnostic images, a first dynamics measure indicative of a contrast agent dynamic through the region of interest over time for the first state, to derive, from the second time series of diagnostic images, a second dynamics measure indicative of a contrast agent dynamic through the region of interest over time for the second state and to determine, based on the first dynamics measure and the second dynamics measure, at least one index indicative of a relative difference between the first state and the second state, and an output unit adapted to output the at least one index to a user.

The invention claimed is:

1. An apparatus, comprising:

a computer configured to provide treatment guidance for an ablation treatment, wherein the computer is configured to:

receive a first time series of diagnostic images representative of a pre-treatment state occurring before the ablation treatment, receive a second time series of diagnostic images representative of a post-treatment state occurring during or after the ablation treatment;

derive, from the first time series of diagnostic images, a first dynamics measure indicative of a contrast agent dynamic over time for the pre-treatment state; and determine at least one index indicative of a relative difference between the pre-treatment state and the post-treatment state, wherein the at least one index is determined using:

the first dynamics measure; and a second dynamics measure based on the second time series and indicative of a contrast agent dynamic over time for the post-treatment state; and output the at least one index to a user.

2. The apparatus of claim 1, wherein at least one of the first time series or the second time series is acquired using X-ray angiography.

3. The apparatus of claim 1, wherein the ablation treatment corresponds to a renal denervation (RDN) treatment.

4. The apparatus of claim 1, wherein the first time series is obtained for a first sub-region of interest for the pre-treatment state such that the first dynamics measure is indicative of the contrast agent dynamic through the first sub-region of interest over time for the pre-treatment state, wherein the second time series is obtained for the first sub-region of interest for the post-treatment state such that the second dynamics measure is indicative of the contrast agent dynamic through the first sub-region of interest over time for the post-treatment state, wherein the computer is configured to:

receive a third time series of diagnostic images obtained for a second sub-region of interest for the pre-treatment state;

derive, from the third time series of diagnostic images, a third dynamics measure indicative of the contrast agent dynamic through the second sub-region of interest over time for the pre-treatment state, and wherein the at least one index is further determined using:

the third dynamics measure; and a fourth dynamics measure based on the second time series and indicative of the contrast agent dynamic through the second sub-region over time for the post-treatment state.

5. The apparatus according to claim 1, wherein at least one of the first time series or the second time series are acquired using one or more predetermined acquisition settings.

6. The apparatus of claim 1, wherein the computer is configured to receive additional patient data, and wherein the at least one index is further determined using the additional patient data.

7. The apparatus of claim 1, wherein, to derive the first dynamics measure from the first time series of diagnostic images, the computer is configured to:

derive, for each point in time, a value for the first dynamics measure; and represent the values for the first dynamics measure as a function of time.

8. The apparatus of claim 1, wherein, to determine the at least one index, the computer is configured to analyze, for the pre-treatment state and the post-treatment state, at least one of:

an arrival time of the contrast agent, a wash in rate of the contrast agent, a wash out rate of the contrast agent a time to peak of at least one of the first dynamics measure or the second dynamics measure, a duration of peak of at least one of the first dynamics measure or the second dynamics measure, a peak value of at least one of the first dynamics measure or the second dynamics measure, an average peak value of at least one of the first dynamics measure or the second dynamics measure, or an area under a curve representing values for at least one of the first dynamics measure or the second dynamics measure, as a function of time.

9. The apparatus of claim 1, wherein the computer is configured to:

generate an indication comprising one or more of a visual, auditory, haptic or audiovisual indication; and output the indication to the user.

10. The apparatus of claim 1, wherein the second time series is derived from a clinical study.

11. The apparatus of claim 1, wherein the computer is configured to compare the at least one index to a predefined threshold value.

* * * * *